United States Patent [19]

Gottesman et al.

[11] Patent Number: 5,053,043
[45] Date of Patent: Oct. 1, 1991

[54] SUTURE GUIDE AND METHOD OF PLACING SUTURES THROUGH A SEVERED DUCT

[75] Inventors: James E. Gottesman, Mercer Island, Wash.; Thomas L. Foster, Poland, Ind.

[73] Assignee: Vance Products Incorporated, Spencer, Ind.

[21] Appl. No.: 590,178

[22] Filed: Sep. 28, 1990

[51] Int. Cl.⁵ .............................................. A61B 17/00
[52] U.S. Cl. ..................................... 606/148; 128/898
[58] Field of Search .......................... 606/148; 128/898

[56] References Cited

U.S. PATENT DOCUMENTS

| | | | |
|---|---|---|---|
| 3,908,637 | 9/1975 | Doroshow | 128/2 F |
| 4,848,367 | 7/1989 | Avant et al. | 128/898 |
| 4,873,977 | 10/1989 | Avant et al. | 128/334 R |
| 4,911,164 | 3/1990 | Roth | 606/148 |

Primary Examiner—Stephen C. Pellegrino
Assistant Examiner—Gary Jackson
Attorney, Agent, or Firm—Richard J. Godlewski

[57] ABSTRACT

A suture guide and, in particular, a urethral sound having interchangeable tips for placing sutures in the severed end of a body duct. The urethral sound includes an attachment mechanism having interconnection parts longitudinally rotatable when interconnected. The sound further includes an elongated member having a distal end portion including one of the interconnection parts. A plurality of interchangeable tips are provided each having a rounded distal end and a proximal end including the second interconnection part. Interchangeable tips are positioned at the distal portion of the elongated member and are longitudinally rotated thereat. Various tips include one or more apertures for placing sutures through, for example, a severed urethral stump created during a radical prostatectomy. Channels are also placed in a number of the tips to provide placement of individual sutures about the distal end of the severed stump as desired by the physician. The method includes positioning the urethral sound tip out the distal end of the duct with an aperture in the tip partially protruding from the duct. A suture thread is passed through the aperture and cut to form two equal length suture pieces on the opposite sides of the duct. The urethral sound tip is rotated to further position additional suture pieces about the severed end of the duct. The pieces are formed by cutting the suture extending through the aperture at the mid-point thereof.

20 Claims, 3 Drawing Sheets

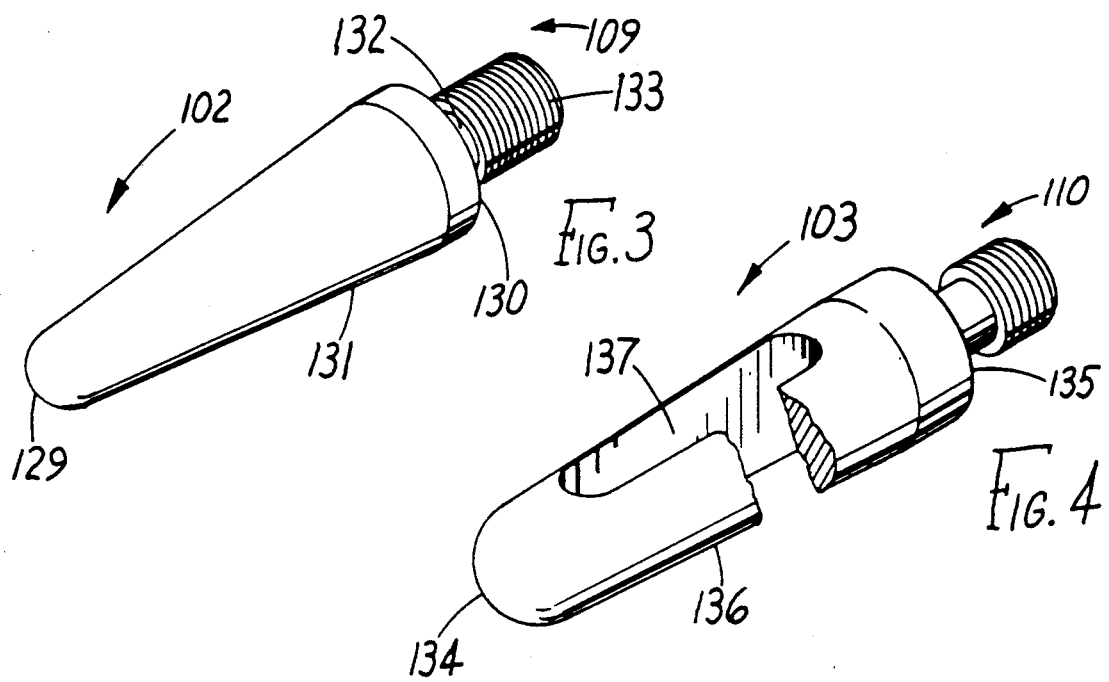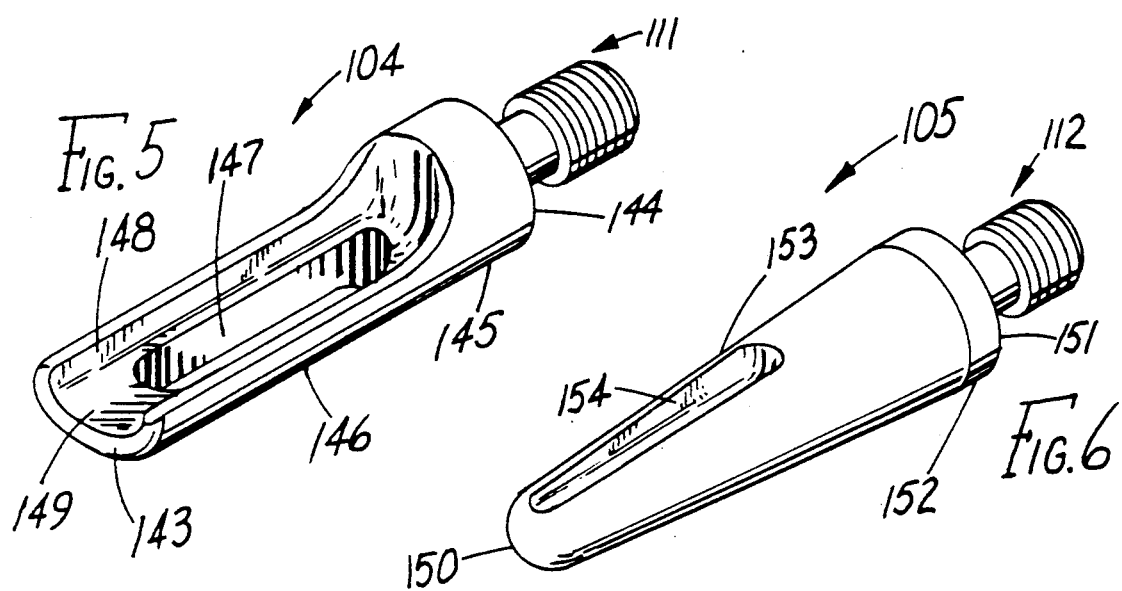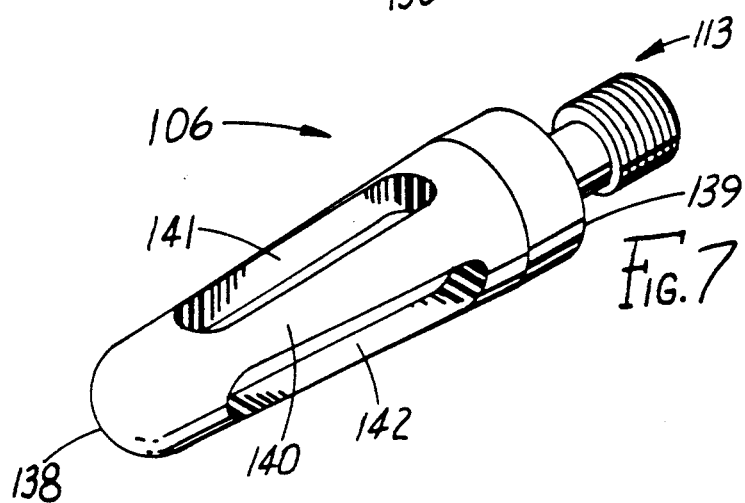

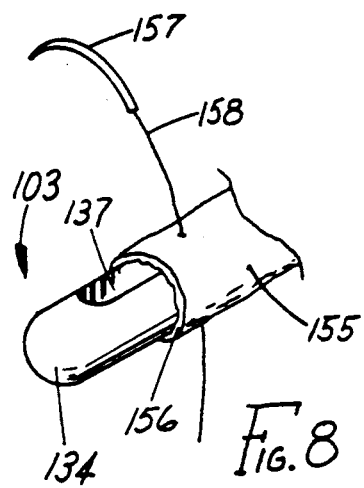
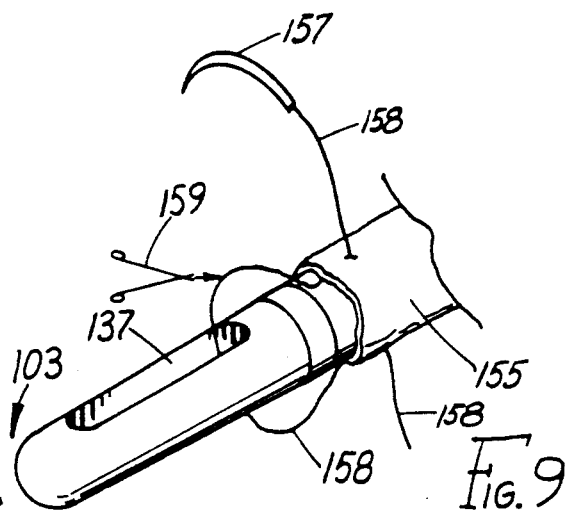
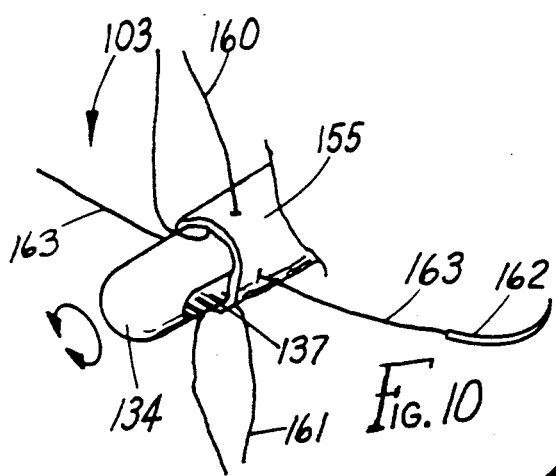
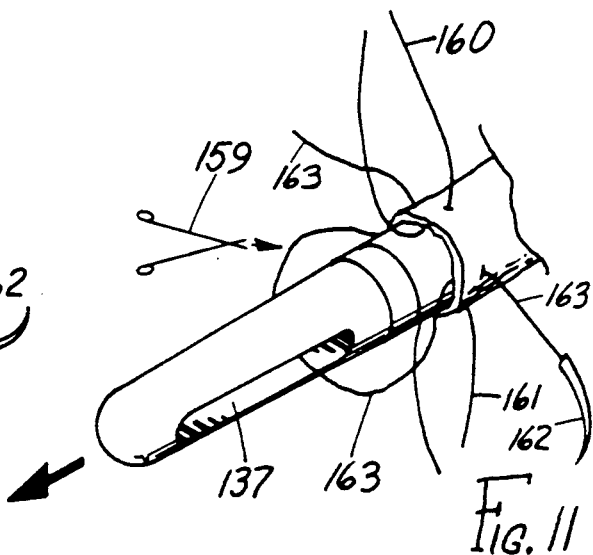
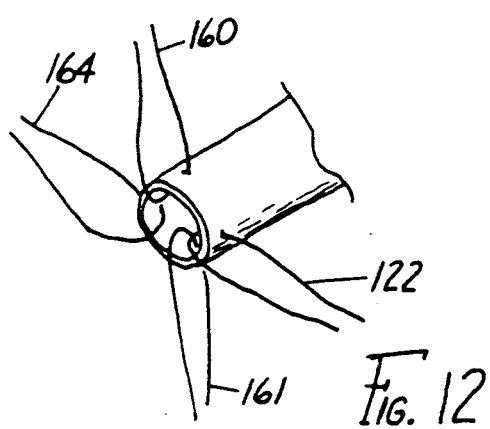

SUTURE GUIDE AND METHOD OF PLACING SUTURES THROUGH A SEVERED DUCT

TECHNICAL FIELD

This invention relates to suture guides and particular, a suture guide and method of placing sutures through the severed end of a duct.

BACKGROUND OF THE INVENTION

A radical prostatectomy is an effective procedure for the treatment of patients with localized carcinoma of the prostate gland. The placement of sutures into the urethral stump after the removal of the prostate is among the more difficult surgical procedures facing urologists. The angle that the urethral stump creates with the pelvic floor, the depth of the pelvis, and the retractability of the urethral stump make passage of a suture in or out of the urethra a test of surgical skill. Urethral sounds, perineal pressure, and tractioned moving catheters are often helpful but not a ready solution.

Prior art urethral suture guides commonly include longitudinal grooves or channels in the surface thereof about the distal end for guiding a needle in suture placement. However, suture placement in the urethral stump still remains difficult.

SUMMARY OF THE INVENTION

The foregoing problems are solved and a technical advance is achieved with an illustrative surgical guide comprising a cylindrical member having a distal tip including an elongated body and an aperture extending laterally through the body for the placement of a suture through opposite sides of the severed end of a urethral duct. The cylindrical member includes a proximal end portion with a handle positioned about and extending longitudinally therefrom. The tip extends from the distal end portion of the cylindrical member and has a rounded distal end which is inserted through the urethral meatus and pushed therethrough to extend the urethral stump from the adjacent surrounding tissue. The tip of the guide is pushed out of the urethral stump with the aperture partially appearing therefrom for positioning sutures illustratively in the 9 and 3 o'clock positions. After the aperture is placed in the desired position, a needle with a suture attached is passed through one side of the urethral stump about the severed end, through the suture guide aperture, and out the opposite side of the duct. The suture is advantageously extended beyond the severed end of the duct by pushing the tip of the guide with the suture positioned therethrough out the severed end of the duct. The suture extends through opposite sides of the duct as well as the suture guide aperture to form two equal length suture pieces on opposite sides of the urethral duct at the illustrative 9 and 3 o'clock positions.

Advantageously, the tip of the suture guide also includes a second aperture extending laterally therethrough and communicating with the first aperture for placing pairs of suture pieces illustratively at the 9, 12, 3, and 6 o'clock positions at the end of the severed urethral duct. In those cases where the urethral stump has been severed extremely close to adjacent tissue or has been occluded, a tip with a semi-cylindrical portion extending longitudinally and proximally from the distal end is utilized. As a result, individual sutures are placed through the duct about the severed end individually at desired positions therearound. An aperture extends through the semi-cylindrical portion with a semi-cylindrical recess formed longitudinally therein for placing individual sutures about the severed end of the duct.

With respect to another aspect of the invention, an illustrative urethral suture guide comprises an attachment mechanism for rotatably interconnecting the tip and the elongated member of the guide. The attachment mechanism includes first and second interconnection parts longitudinally rotatable when interconnected. This advantageously permits the rotation of the tip with respect to the elongated member for placement of sutures through the severed end of the urethral duct. The elongated member includes a substantially straight portion, a distal end portion, and a curved portion positioned between the straight and distal end portions, the distal end portion including one of the interconnection parts. The guide also includes an interchangeable tip having a distal end and a proximal end including the interconnection part. The rotatable, interchangeable tip constitutes a significant improvement over the prior art and allows the tip to be rotated to desired positions about the severed end of the duct for placement of a suture therethrough. Illustratively, one of the interconnection parts includes a receptacle, and the other includes a projection. The projection is selectably positioned in the receptacle to provide interconnection and longitudinal rotation. The projection includes a neck and a head extending longitudinally from and wider than the neck. The receptacle includes a chamber larger than the head and a collar having a passageway larger than the neck and communicating with the chamber. The neck is longer than the passageway of the collar to facilitate the head being positioned in the chamber. The head is shaped for selective passage through the passageway of the collar and into the chamber located, for example, in the distal end portion of the guide. Selective passage is accomplished by a plurality of internal threads extending radially into the passageway of the collar with the head having a second plurality of external sutures extending radially from and matching the internal sutures of the collar. The head is threaded through the passageway of the collar and into the chamber for longitudinal rotation of the tip with respect to the elongated member of the guide. The neck, being longer and smaller than the passageway of the collar, does not engage the internal threads further facilitating easy rotation of the tip and elongated member of the guide.

The interchangeable tip advantageously includes a number of different configurations. A first tip includes a cylindrical body extending longitudinally between the distal end and the proximal end of the tip. The body includes a first aperture extending laterally therethrough for the placement of sutures through opposite sides of the urethral duct about the severed end.

In another aspect of the invention, a second tip includes an elongated body having first and second apertures, both of which extend laterally through the body and communicate with each other. The criss-crossed apertures facilitate placement of sutures 90 degrees apart about the severed end of the duct.

In another aspect of the invention, the tip includes an elongated body having a semi-cylindrical portion extending longitudinally between the rounded distal end and the proximal end. The semi-cylindrical portion includes an aperture extending laterally therethrough for the placement of a suture through one side of a severed duct end. To further facilitate easy placement, the semi-cylindrical portion also includes a channel having a semi-cylindrical surface extending longitudinally and proximally from the distal end and communicating with the aperture. The channel advantageously guides the suture needle through the aperture when placing sutures from the inside to the outside of the severed duct end.

In yet another aspect of the invention, the tip includes a tapered, cylindrical body between the distal end and the proximal end thereof. A channel extends longitudinally and proximally from the rounded distal end through the tapered surface of the body.

The method of placing sutures through a severed tubular body duct such as the urethral stump is accomplished by the use of the illustrative suture guide. As previously mentioned, the method comprises positioning the suture guide in the severed duct with the distal end of the tip and the aperture partially protruding from the severed end of the duct. A needle with a suture attached is then placed through one side of the duct about the severed end, through the aperture of the tip, and out the opposite side of the duct. The tip of the suture guide is pushed out the severed end of the duct completely exposing the aperture with the suture extending therethrough. The suture extending through the aperture is cut to form two suture pieces on opposite sides of the duct about the severed end. The rotatable, interchangeable tip is rotated a predetermined angle and positioned once again with the suture guide and the aperture partially protruding from the severed end of the duct. Another suture is passed from one side of the duct, through the aperture and out the opposite side of the duct. The tip and aperture with the suture positioned therethrough are once again pushed out the severed end of the duct. The suture extending through the aperture is cut to form two additional suture pieces on opposite sides of the duct about the severed end.

The method further comprises rotating any of the aforementioned tips a predetermined angle and positioning the suture guide with the aperture partially protruding from the severed end of the duct. Placement of the suture through the sides of the severed duct and aperture is repeated by pushing the distal tip with the suture extending through the aperture out the severed end of the duct and cutting the suture to form two additional suture pieces on opposite sides of the duct about the distal end. In difficult cases where the severed end of the duct is extremely short, the semi-cylindrical portion of the tip may be used to place individual sutures from either the inside to the outside of the duct or vice versa from the outside to the inside of the duct.

BRIEF DESCRIPTION OF THE DRAWING

FIGS. 3-7 depict various interchangeable tips of the urethral suture guide of FIG. 1; and FIGS. 8-12 depict the method of placing sutures through the distal end of a severed body duct.

DETAILED DESCRIPTION

Figure 1:
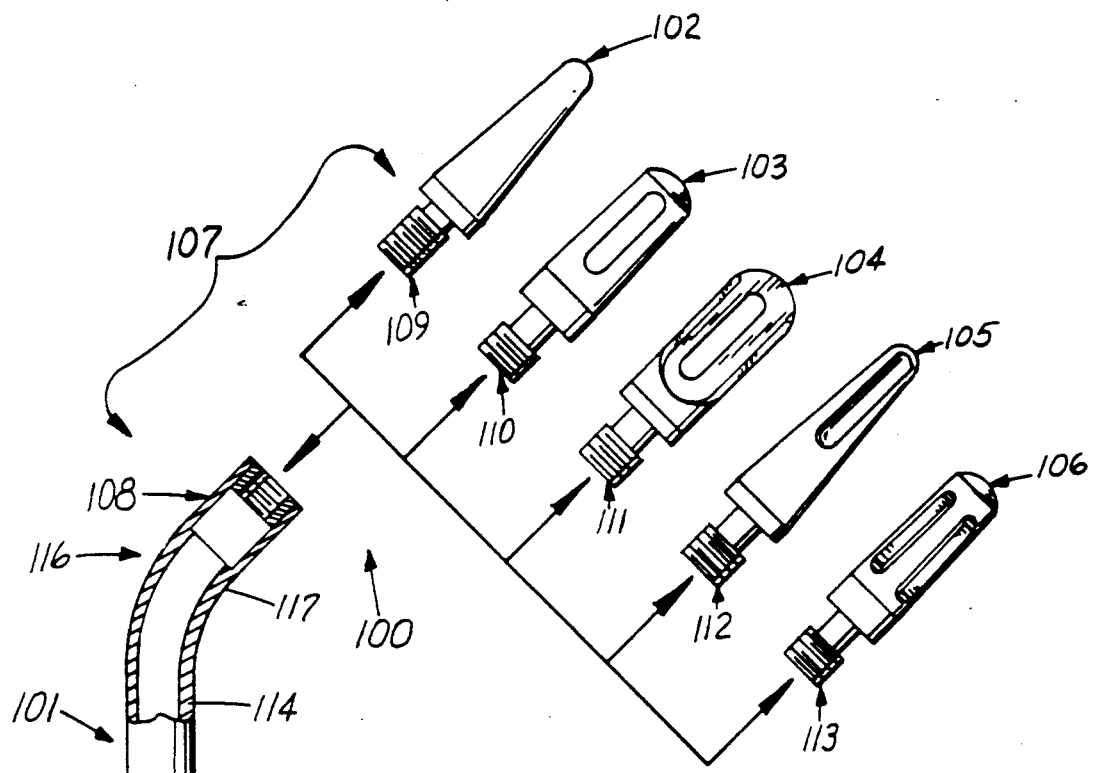
FIG. 1 depicts a preferred embodiment of the urethral suture guide of the present invention.

Depicted in FIG. 1 is a preferred embodiment of suture 15 guide 100 of the present invention. This particular suture guide has application as a urethral sound for suturing the urethral stump to the neck of the bladder during a radical prostatectomy surgical procedure. Urethral sound 100 comprises an elongated member 101 and a plurality of interchangeable tips 102-106 interconnected by attachment mechanism 107. Attachment mechanism 107 includes interconnection parts 108-113 that are longitudinally rotatable when any one of male interconnection parts 110-113 are interconnected with female interconnection part 108.

Elongated member 101 comprises a cylindrical stainless steel tube 114 approximately 8.50" in length with a 0.375" outside diameter and a 16-gauge wall thickness. The cylindrical elongated member tube includes a substantially straight portion 115, distal end portion 117, and a curved portion 116 positioned between the straight and distal end portions. Distal end portion includes interconnection part 108 of attachment mechanism 107. Attached about the proximal end 118 of straight portion 115 is a stainless steel handle 119 as shown. The handle is attached to proximal end 118 using any number of well-known techniques such as press fitting the handle thereon.

Figure 2:
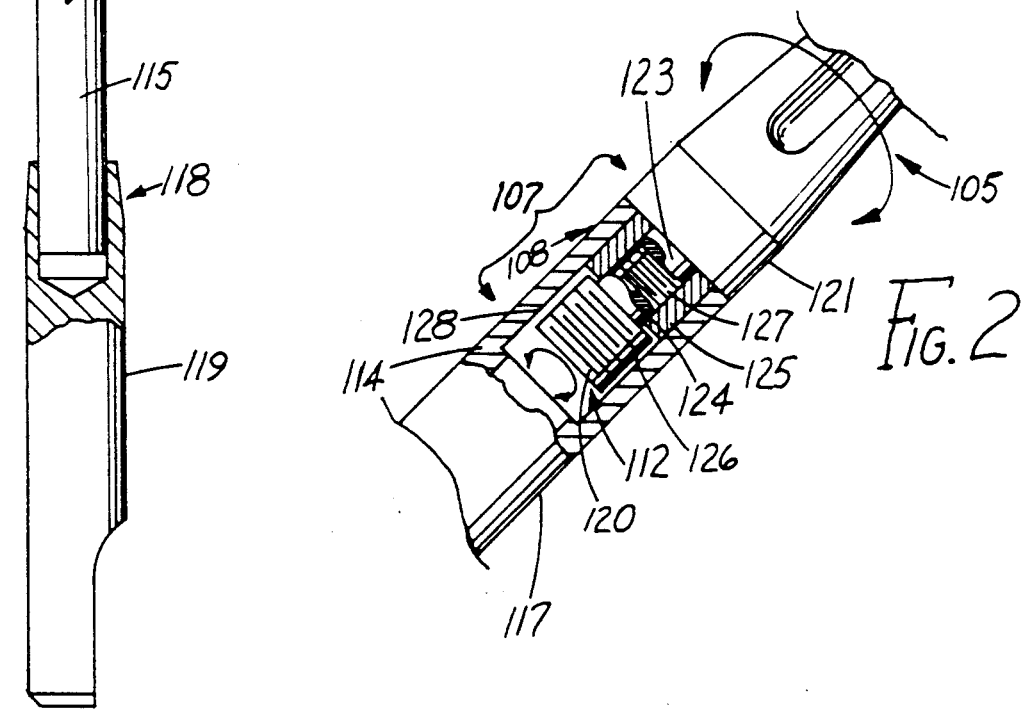
FIG. 2 depicts the attachment mechanism of FIG. 1 with interconnection parts interconnected.

Depicted in FIG. 2 is attachment mechanism 107 with female and male interconnection parts 108 and 112 interconnected. Male interconnection part 112 comprises a projection extending from proximal end 121 of interchangeable tip 105. Projection 112 comprises a stainless steel neck 123 and head 126 which extends longitudinally from and is wider than the neck. The neck is approximately 0.187" in length and 0.155" in diameter. The head is approximately 0.187" in length and 0.208" in diameter with 12-24 external threads 120 formed therein.

Female interconnection part 108 comprises a receptacle for receiving and retaining projection 112 therein. When fully inserted in the receptacle, the projection is longitudinally rotatable in either a clockwise or counterclockwise direction as shown. Receptacle 108 comprises chamber 128 and collar 125 with passageway 124 having 12-24 internal threads 127 formed therein. Chamber 128 is formed by reaming the distal end portion 117 of stainless steel tube 114 to a diameter of 0.302" and a depth of approximately 0.500". Collar 125 is inserted into the distal end of the tube and positioned thereat with, for example, silver solder. The length of collar 125 is approximately 0.175" which is shorter than the length of neck 123. This facilitates the free rotation of neck 123 within passageway 124 when head 126 is fully inserted in chamber 128. The diameter of threaded passageway 124 is larger than that of neck 123 for providing free rotation of the neck in the passageway.

To insert threaded head 126 into chamber 128, the head is turned through threads 127 of collar passageway 124. After the head is fully threaded through passageway 124, the head is fully positioned in chamber 128 and is freely rotatable therein.

Depicted in FIGS. 3-7 are pictorial views of interchangeable tips 102-106, respectively. FIG. 3 depicts urethral sound tip 102 with rounded distal end 129, proximal end 130, and male interconnection part 109 extending longitudinally therefrom. Sound tip 102 includes a tapered cylindrical body 131 extending between the rounded distal end and the proximal end. The tapered body of the tip dilates a urethral duct as the sound is inserted therethrough. Male interconnection part 109 comprises neck 132 with threaded head 133 extending longitudinally and proximally therefrom. Threaded head 133 is approximately 0.312" in length for engaging collar passageway threads 127 when inserted in receptacle 108. The 12-24 threads of head 133 fixedly position sound tip 102 to the distal end portion of elongated member 101. As a result, sound tip 102 does not rotate freely when fully inserted into receptacle 108. When urethral sound 100 is fully inserted through the urethral duct with tip 102 extending distally therefrom, the tip is removed and one of the other tips 103-106 is inserted in the distal end portion of the elongated member for placing suture threads in the severed end of the urethral duct.

FIG. 4 depicts urethral sound tip 103 having rounded distal end 134, proximal end 135, and male interconnection part 110 extending longitudinally and proximally therefrom. Urethral sound tip 103 also includes a cylindrical body 136 extending longitudinally between the rounded distal end and the proximal end. The overall length of each of the urethral sound tips is approximately 1.625". The proximal end of each is approximately 0.375" in diameter. The urethral sound tips are formed from any rigid biocompatible material such as 300 series stainless steel. Tip body 136 of urethral sound tip 103 has an approximate 2 degree taper thereto with distal tip 134 having a 3/16" radius. Cylindrical body 136 has an aperture 137 extending laterally therethrough. The aperture is an elongated slot having a 3/32" radius curvature at each end with a straight portion of 0.375" in length. When urethral sound tip 103 is protruding from the severed distal end of the urethral duct with aperture 137 partially extending therefrom, the physician passes a curved suture needle with thread attached through one side of the urethral duct, through aperture 137, and out the opposite side of the severed urethral duct end. Aperture 137 guides the needle through the duct to position suture pieces on opposite sides of the severed end of the duct.

FIG. 7 depicts urethral sound tip 106 that is similar to urethral sound tip 103. Urethral sound tip 106 includes distal end 138, proximal end 139, and male interconnection part 113 extending longitudinally and proximally therefrom. Cylindrical body 140 extends longitudinally between the rounded distal end and the proximal end of the tip. The dimensions of the tip are similar to those described with respect to urethral sound tip 103. The body is slightly tapered between the rounded distal end and the proximal end thereof. The body of the tip also includes first aperture 141 extending laterally therethrough. A second aperture 142 also extends laterally through the body and communicates with aperture 141. The two apertures facilitate the placement of two suture threads concomitantly through the severed end of the urethral duct. As a result, suture thread can be illustratively positioned at the 9, 12, 3, and 6 o'clock positions of the severed end of the urethral duct. The sutures are positioned in the apertures just outside the severed end of the duct to form four suture pieces which are used to interconnect the severed duct end and the bladder neck. Interconnection part 113, as well as that of interconnection part 110 of urethral sound tip 103, is similarly dimensioned as described with respect to interconnection part 112 of tip 105.

FIG. 5 depicts urethral sound tip 104 having rounded distal end 143, proximal end 144 and male interconnection part 111 extending longitudinally and proximally therefrom. Urethral sound tip 104 includes elongated body 145 extending longitudinally between the rounded distal end and the proximal end. The elongated body includes a semi-cylindrical portion 146 extending proximally from the rounded distal end 143. The semi-cylindrical portion 146 includes aperture 147 extending laterally therethrough and further includes a channel 148 having a semi-cylindrical surface 149 extending longitudinally and proximally from the rounded distal end and communicating with aperture 147. The semi-cylindrical portion of urethral sound tip 104 facilitates the placement of individual sutures about the severed end of the urethral duct. The suture needle is placed in the semi-cylindrical surface channel for placing sutures from inside the duct to the outside surface thereof. The surgeon rotates the sound tip as previously described to position the suture threads as desired. This is particularly useful where the severed end of the duct is surrounded by adjacent tissue or has been cut well into the urogenital diaphragm. Interconnection part 111 is also similarly fashioned as described with respect to interconnection part 112 of urethral sound tip 105.

FIG. 6 depicts urethral sound tip 105 having rounded distal end 150, proximal end 151, and interconnection part 112 extending longitudinally and proximally therefrom. This tip is utilized by the physician to again place individual sutures about the severed end of the duct as desired by the physician. The tip includes cylindrical elongated body 152 extending longitudinally between the two ends 150 and 151 and includes a tapered cylindrical surface 153. The surface includes approximately a 5 degree taper with respect to cylindrical elongated body 152. The rounded distal end has a 3/32" radius similar to that of urethral sound tip 102. A narrow channel 154 extends proximally through tapered cylindrical surface 153 and from the rounded distal end and is approximately 0.12" in depth with respect to the diameter of cylindrical body portion 152.

FIGS. 8-12 depict the method of placing suture threads through a severed tubular body duct by means of the aforementioned suture guide, in particular, urethral sound 100. As shown in FIG. 8, interchangeable tip 103 protrudes from the severed end 156 of urethral duct 155. The method comprises positioning the tip of the suture guide into the severed duct with rounded distal end 134 protruding from the severed end of the duct. Aperture 137 also partially protrudes from the severed end of the duct with the remaining portion of the aperture positioned in the passageway of the duct for the placement of curved suture needle 157 and suture thread 158 therethrough. The method comprises placing the needle and suture thread through one side of the duct about the severed end, through the aperture of the tip, and out the opposite side of the duct. The midpoint of the suture is centered in the aperture.

As depicted in FIG. 9, the method further comprises pushing the urethral sound tip out the severed end of the duct with aperture 137 fully exposed and suture thread 158 extending therethrough. The suture thread is cut about aperture 137 with, for example, scissors 159. The suture thread is cut at the midpoint thereof to form two equal length suture pieces on opposite sides of the duct about the severed end. Equal length suture pieces 160 and 161 are depicted in FIGS. 10-12.

The method further includes rotating interchangeable tip 103 a predetermined angle, in particular, 90 degrees for placing four sutures at the severed end of the duct. As shown in FIG. 10, the aperture is placed at the 9 and 3 o'clock positions with suture pieces 160 and 161 illustratively positioned at approximately the 12 and 6 o'clock positions of the severed end of the duct. Again, the tip is positioned with distal end 134 and aperture 137 partially protruding from the severed end of the duct. The procedure further includes placing curved suture needle 162 with suture thread 163 attached through one side of the duct of the severed end, through the aperture, and out the opposite side of the duct. The midpoint of the suture is again centered in the aperture.

As shown in FIG. 11, the method further includes pushing the tip out the severed end of the duct with aperture 137 protruding completely therefrom. Suture 163 is also extended from the distal end of the duct. Suture thread 163 is then cut with, for example, scissors: 159 to form two additional equal length suture pieces 164 and 122 on opposite sides of the duct about the severed end as depicted in FIG. 12.

This procedure is continued to place additional suture pieces about the severed end of the duct as desired. Alternatively, urethral sound tips 104 and 105 may be utilized by the physician to place individual suture pieces about the severed end of the duct as desired in various positions.

After the suture pieces are placed about the severed end of the duct, the physician sutures, in a well-known manner, the suture pieces extending from the severed duct end to the bladder stump.

It should be understood that the aforementioned urethral suture guide and the method of use are merely illustrative of the application of the principles of this invention and that numerous other suture guides may be devised by those skilled in the art without departing from the spirit and scope of the invention. In particular, the nonrotatable tip at the distal end of the urethral sound is formed with a number of apertures extending entirely therethrough and communicating with each other to position suture pieces about the severed end of the duct. Other channels formed in the tip and communicating with the apertures are also contemplated. Furthermore, the attachment mechanism may also include a keyway extending through the collar passageway wall and a head including a projected key capable of moving through the keyway and into the larger chamber of the receptacle. A spring-loaded ball may also be positioned laterally at the end of the projection neck to facilitate placement and rotation within the attachment receptacle. Other forms of attachment mechanism in which the head is selectively positioned through the collar and into the receptacle passageway are also contemplated. It is further contemplated that the tip may be larger in diameter than the elongated member. For example, the diameter of the tip would be 28 French and the diameter of the elongated member would be 24 French. In such an aspect of the invention, the sound is inserted with the tip being the same diameter as the elongated member. Then the tip of the same diameter is exchanged for a tip of a larger diameter for better presentation to the severed end of the duct. The proximal end of the tip is tapered to match the diameter of the elongated member so as not to present a rough or blunt edge about the severed urethral duct end, thereby preventing trauma thereto.

What is claimed is:

1. A urethral suture guide comprising:
   an attachment mechanism having first and second interconnection parts freely longitudinally rotatable when interconnected;
   an elongated member having a substantially straight portion, a distal end portion, and a curved portion positioned between said straight and distal end portions, said distal end portion including said second interconnection part; and
   an interchangeable tip having a distal end and a proximal end including said first interconnection part.

2. The sound of claim 1 wherein said tip includes a cylindrical body extending longitudinally between said distal end and said proximal end.

3. The guide of claim 2 wherein said tip includes a first aperture extending laterally therethrough.

4. The guide of claim 3 wherein said tip includes a second aperture extending laterally therethrough and communicating with said first aperture.

5. The guide of claim 1 wherein one of said first and second interconnection parts includes a receptacle and the other of said parts includes a projection, said receptacle and said projection being interconnected and longitudinally rotatable when said projection is selectively positioned in said receptacle.

6. The guide of claim 5 wherein said projection includes a neck and a head extending longitudinally from and wider than said neck and wherein said receptacle includes a chamber larger than said head and a collar having a passageway larger than said neck and communicating with said chamber, said neck having a length longer than said passageway of said collar, said head being shaped for selective passage through said passageway of said collar and into said chamber.

7. The guide of claim 6 wherein said collar has a plurality of internal threads in said passageway and wherein said head has a plurality of external threads matching said internal threads.

8. The guide of claim 1 wherein said tip includes an elongated body having a semi-cylindrical portion and extending longitudinally between said distal end and said proximal end.

9. The guide of claim 8 wherein said semi-cylindrical portion includes an aperture extending laterally therethrough.

10. The guide of claim 9 wherein said semi-cylindrical portion also includes a channel having a semi-cylindrical surface extending longitudinally and proximally from said distal end and communicating with said aperture.

11. The guide of claim wherein said tip includes an elongated body having a tapered cylindrical surface and extending longitudinally between said distal end and said proximal end and a channel extending longitudinally and proximally from said distal end and through said tapered cylindrical surface.

12. A suture guide comprising:
    a cylindrical member having a proximal end portion, a distal end portion, a substantially straight portion extending longitudinally between said end portions, and a distal tip said distal tip including an elongated body and a first aperture extending laterally through said elongated body; and
    a handle positioned about and extending longitudinally from said proximal end portion of said cylindrical member.

13. The suture guide of claim 12 wherein said elongated body includes a second aperture extending laterally therethrough and communicating with said first aperture.

14. The suture guide of claim 12 wherein said elongated body includes at least a semi-cylindrical portion extending longitudinally and proximally from a distal end of said tip, said first aperture extending through said semi-cylindrical portion.

15. The suture guide of claim 14 wherein said semicylindrical portion includes a semi-cylindrical channel extending longitudinally and proximally from said distal end and communicating with said first aperture.

16. A urethral sound comprising:
an attachment mechanism having first and second interconnection parts longitudinally rotatable when interconnected, one of said parts including a receptacle and the other of said parts including a projection, said receptacle and said projection being interconnected and longitudinally rotatable when said projection is selectively positioned in said receptacle, said projection including a neck and a head extending longitudinally from and wider than said neck, said receptacle including a chamber larger than said head and a collar having a passageway larger than said neck and communicating with said chamber, said neck having a length longer than said passageway of said collar, said head being shaped for selective passage through said passageway of said collar and into said chamber, said collar having a plurality of internal threads in said passageway; said head having a plurality of external threads matching said internal threads;
an elongated cylindrical member having a substantially straight portion, a distal end portion, and a curved portion positioned between said straight and distal end portions, said distal end portion including said second interconnection part;
a handle positioned about and extending longitudinally from said proximal end portion of said cylindrical member;
an interchangeable first tip having a rounded first distal end, a first proximal end including said first interconnection part, and a tapered cylindrical body extending longitudinally between said first ends and having an aperture extending laterally therethrough;
an interchangeable second tip having a rounded second distal end, a second proximal end including said first interconnection part, and a cylindrical body extending longitudinally between said second ends and having first and second apertures extending laterally through said body and communicating with each other; and
an interchangeable third tip having a rounded third distal end, a third proximal end including said first interconnection part, and a cylindrical body extending longitudinally between said third ends and having a semi-cylindrical portion including a third aperture extending laterally therethrough and a channel having a semi-cylindrical surface extending longitudinally and proximally from said third distal end and communicating with said third aperture.

17. A method of placing sutures about a severed end of tubular body duct with a suture guide, said suture guide comprising:
an elongated cylindrical member having a substantially straight portion and a distal end portion including a second interconnection part; and
an interchangeable tip having a distal end, a proximal end including a first interconnection part longitudinally and rotatably interconnected with said second interconnection part, and a cylindrical body extending longitudinally between said ends and having an aperture extending laterally therethrough; said method comprising:
positioning said suture guide into said duct with said distal end of said tip completely protruding and said aperture partially protruding from said severed end of said duct;
placing a needle with a suture attached thereto through one side of said duct about said severed end, said aperture, and out the opposite side of said duct;
pushing said tip and said aperture with said suture extending therethrough out of said severed end of said duct; and
cutting said suture extending through said aperture to form two suture pieces on opposite sides of said duct about said severed end.

18. The method of claim 17 further comprising rotating said interchangeable tip a predetermined angle and positioning said suture guide with said aperture partially protruding from said severed end of said duct.

19. The method of claim 18 further comprising placing a needle with another suture through one side of said duct about said severed end, said aperture, and out the opposite side of said duct;
pushing said tip and said aperture with said other suture placed therethrough out of said severed end of said duct; and
cutting said other suture extending through said aperture to form two additional suture pieces on opposite sides of said duct about said severed end.

20. The method of claim 19 further comprising rotating said tip a predetermined angle;
positioning said suture guide with said aperture partially protruding from said severed end of said duct; and
repeating said placing, pushing, and cutting steps with yet another suture to form two more suture pieces on opposite sides of said duct about said severed end.

* * * * *